United States Patent [19]
King et al.

[11] Patent Number: 6,131,578
[45] Date of Patent: Oct. 17, 2000

[54] INHIBITORS OF UDP-G1CNAC:GA1β1-3GA1NACαR β1-6 N-ACETYLGLUCOSAMINYLTRANSFERASE (CORE 2 G1CNAC-T) AND USE OF THE INHIBITORS TO PREVENT OR TREAT CARDIOMYOPATHY ASSOCIATED WITH DIABETES

[76] Inventors: George L. King, 101 Centre St., Dover, Mass. 02030; Yoshihiko Nishio, 9-12-601 Ichiriyama, Ohtsu, Shiga 520-21; Daisuke Koya, 30 Matsunoki-cho, Shimogamo, Sakyo-Ku, Kyoto 606, both of Japan; James W. Dennis; Charles E. Warren, both of c/o Mount Sinai Hospital, Toronto, Ontario, Canada, M5G 1X5

[21] Appl. No.: 08/943,058

[22] Filed: Oct. 2, 1997

Related U.S. Application Data

[60] Provisional application No. 60/046,876, Oct. 2, 1996.

[51] Int. Cl.[7] .................................................. A61B 19/00
[52] U.S. Cl. ............................................. 128/898; 424/278
[58] Field of Search .......................... 128/898; 424/278, 424/94.1, 184.1, 185.1, 193.1

*Primary Examiner*—Mickey Yu
*Assistant Examiner*—Kelly O'Hara
*Attorney, Agent, or Firm*—Merchant & Gould P.C.

[57] ABSTRACT

Cardiomyopathy associated with diabetes and hyperglycemia can be treated by administering to a subject suffering from this condition a substance that inhibits UDP-GlcNAc:Galβ1-3GalNAcαRβ1-6-N-acetylglucosaminyl transferase (core 2 GlcNAc-T) activity.

10 Claims, 11 Drawing Sheets

Differential Display

Clone    DH 1            13

Northern Blot Analysis

28S —
18S —

36B4

C D C D          C D C D
Heart Aorta      Heart Aorta

FIG. 3A

```
                                                                                          A  -801
GTTCAGCAAGGCCTTTTAAGTCCATTTTGAATACTCAGCAGAATGAATTGTCTTGCTTCCAGATGTGTGGATCACATTCACGATTGTTCTTAACCTTTTT    -701
CTCTAAAGTGAGTCACCGTCCTAAGTCAGCAAAAGGCAGAATGGATCTGACCCTTGCAAGCGTCTTCTGCCTGTTGATGTCACCAGGAGGAACTTGGTGA    -601
CGATATGAAGATAGAGGTGCTGATTCTTAGGACCTGCAGAGTCCTGTGCTCCTGTATAGCCATAGGTCCAGCTTTTGAGACAGTTTCTTTTTTTATAGTC    -501
CTGGTTGTCCTGGAACTCACTACATAGACCAGACTTGCCTCTGCCCCCTAGGTGCTGGGATAAAGGTGTGTGTTACCTCGTGGGATCTCAGATGTCTATG    -401
GTAGGATATTTTAGGACGTCCTTGTTTTAGGTTCGGTGCCTATTTTTACCCCCAGTTTCCGGCTTCAATTTGAGAACAATGGGTCTTCTATGAAGCGATC    -301
TCTATTCTCTAATTAAGACAACCTCTTTTTTTTTTTTTTTTTCTAAATAAAATCTGGTCTCATAGCAAAGGGGATAGTTTTGAGCCTGAGAAGACGCTGT    -201
AAACAGTTGCATTTACTAAGTGTGTTCTTTGCTATATTTTCTTTTGCTTTTAGCTCTGTCCTGTGTGGTGCTCTATTGTCCCTCTTACAAACTGGCAACT    -101
TATCTGGCCACAACAGAAGGACACTGGAGGAAACCTCACTGGCGTCCAAGGCCTAGAAGATTGTTCCACCACCCCAGGGAGCCTCTGAGTGTTCTTTGAA    -001
ATGCTGAGAAACTTGTTTCGGAGGAGACTTTTTTCTTATCCTACAAAATACTACTTCATGGTTCTTGTTCTGTCTCTAATTACCTTCTCTGTTGTAAGAA     100
TTCATCAGAAGCCTGAATTTGTTAGTGTCAGTCACTTGGAGCTTTCTGGAGATGATCCCAATAGCAATGTTAATTGCACCAAAGTTTTACAGGGTGACCC     200
AGAAGAAATCCAGAAGGTGAAGCTTGAGATACTAACAGTGCAATTCAAGAAGCGTCCGAGGCGGACACCGCATGACTATATAAACATGACCCGGGACTGC     300
GCCTCCTTCATCAGGACACGCAAATATATTATGGAGCCCCTTACTAAAGAAGAGGTTGGCTTTCCAATTGCATATTCCATAGTGGTTCATCATAAGATTG     400
ACATGCTTGACAGGCTCCTGAGGGCCATCTATATGCCACAGAATTTCTACTGCATTCACGTGGACAGAAAAGCAGAGGAATCCTTTTTAGCCGCGGTGCA     500
GGGCATTGCATCCTGCTTTGATAATGTCTTTGTGGCCAGCCAGTTGGAGAGTGTTGTATACGCCTCCTGGAGTCGGGTTAAGGCTGACCTCAACTGCATG     600
AAGGACCTGTACAGAATGAATGCAAACTGGAAGTACTTGATCAATCTTTGTGGTATGGATTTCCCTATTAAAACCAACCTGGAAATTGTCAGGAAGCTCA     700
AGTCCTTCACAGGGGAAAACAGCCTGGAAACTGAGAAGATGCCTCCCAACAAGGAAGAGAGGTGGAAAAAAACGATACACGGTTGTGGACGGGAAGCTGAC     800
AAACACTGGAGTTGTCAAGGCGCAGCCTCCACTCAAAACTCCTCTCTTTTCAGGCAGCGCCTATTTCGTGGTCACTAGGGAATATGTAGGCTATGTGCTG     900
GAAAATAAAAATATTCAAAAGTTCATGGAATGGGCACAGGACACATACAGCCCGGATGAGTTCCTCTGGGCCACCATCCAAAGGATCCCTGAAGTCCCTG    1000
GTTCTCTCCCCTCAAGCCATAAGTATGACTTGTCTGACATGAATGCTGTCGCTAGGTTTGTCAAGTGGCAATACTTCGAAGGCGATGTTTCCAATGGCGC    1100
GCCTTATCCACCGTGCAGTGGAGTCCATGTGCGCTCTGTGTGCGTCTTTGGAGTTGGTGACTTGAGCTGGATGCTGCGCAAACACCACTTTTTTGCCAAT    1200
AAGTTTGACATGGATGTGGATCCCTTTGCCCTCCAGTGTTTGGAGAACATCTGAGGCATAAAGCCCGGAGACCTTAGAACGCTAAGCACTGTTGGCAG     1300
TCCTGGGGAAGATAAAGACACACAAGCTGTACCCTCATCTGCTTCCCTTCTCTCCTATCGGGTCCTCCTATTGGGGCGATGACTTCAAAGTCTTCCTGTC    1400
AGGGAAGCTGCGTGGATCCTACAGAACATAGCTACAAGAGAGATTGATACATTGCGTGCTCTAGAGTAAATGCAAGGACGGAGTTAGGATGGCTGGAGGC    1500
TGGGGAAGATTTTGTGGACAGAGAGGCTCTGGGTAATTGAGAAAGAGGCCAATGAAAAGCGTCAGCCTTGAGAACTAATCAAAGAACCCAGGTACTTAAT    1600
CTAAATGAGATTTGATTTGTGCCAAAAGTCGCTTGAAAACGTTAAGCATAATTTTCTTGACAGGAATAAATTTGTAGCAACAACCAATCACAGAGATAGG    1700
ATTTCTCTTGTATGTTTTTTGGAACAGACGTTTGGTCTTACTCTAACTTATCCTTGTAAATAATTTCCTTCCTGCTGTGATTTTGGGTAGGGGGTCTCAG    1800
GGAGCTTAAAATATGTTTGGCATGAATAGCTCTGTCTTAATTTTCGCTTATAACTACACATACATGTTTCAAAAGCAAGAGGACAGTTTCTAGTTCCCGA    1900
CTTCTTTGAGTATTCCTTTATTAAAAAGAACCAGCTGGGTGTGTCACCTGTGCCTGTGAAGCAGGGCAGTTGTTTAATCTCGAGTGATATCGGCCAAGC    2000
TGGACAACAAAACAAGAAGTTGTCTCTTTAAAAAGGAGAAGAAGATCAACTCGATTTTACAAATACATAGTTTTTTCCTTATCTTGTCTTCCCGACTGCT    2100
TATACTGTCAAGCTGCACACATGTCGCTGTTTAAGGACCCTATATCTGTGTTTTGGGTCTTCGATGGGAACCAGTCACCTGTAACTAGTGCAAAAAATTA    2200
GGGAGGGTGAAGTAGGCATCCAAGGGGAGATGGGAATCTACTAAGGCTGTTGCTAAGCCCCTGGCACAAGTTTTGTCCCAAGAAATTAAGGTTTCTGCCT    2300
ACTGGATCCGATTGTGTCTCATGTGGCCACATTCTGGCCTTGAGTATTCATGTTATCTGCCCATTGGCTTTTCTTAACCTGCCAGTTTCCTCCTCTCTCA    2400
CGGCCTTGATGAGGGGGAAAGAAGTAGAGAAAAATGCCTGTGTCCACACTAAGTGTTTGAAAAGAGTTGTGGTATCATAATATGTTTTCACCAAAAGACA    2500
AACGGTCTAGGGTTTCTTCAACTCTTTCTCTTGTCTCTAGTGCAGGGTTGTTTGTTTGTTTTCTCTTAATATTTAGCTAAATCTAAACAGGATTCTAGTG    2600
AAATGTGAAGACTTGCCATTTGATTTTAAATAAGAATCATTACCACGTACTTTCATTTACTTTCATAATCCAGAAGAAAATCATAGTATCAGACAGTTTT    2700
AAGGTATTCAGCAGAGAAAGTGTGTTTTCTGCCTCTTTGCTATGAAGTGTTTTAGGATCAGGAGATAAGCTGGGTTTTGTGTTGGACCAATAGAAATGCG    2800
TTTGCCACAGGGTCACCAGCGATGATGGCGGTGCCATGGACGCCATCTACACAATCTGGCTTCTGGCTTCTGCTTTCTTTTTAGTTGTAACCAAGATTGT    2900
CCAATGGTCCTTTTAGTAGAAAGGCTTTTACTTATGAAGACAGGGCATCTTTTAAATCTAAAACCAGTGGTACCTGGTGACATATCATTTGGGTAAGCCG    3000
CTGTGACTTCAGCAGATTTTCTTTTTCCATCTTGAAAGTGCAGGGTTAAAGCAGTAGTCTTGGGATCAACAAACGGCAACCCCAACCTGGGGTAGCCGG    3100
TGGTCAACACATCCAGCCCGATTTGCTTTATACTCAATGAGCTCTTGAACTTTCCAAAACTGGAAATTTTTTTTTAATTACAAGTACTTTTTTTCTTAA    3200
AAAAAAATCAACTATTTGATGTTATTCATCTAAACACTCTTAATTGTAGTGGTGCTCCATTTCAGTTAAATGCAAGTTTGAGGATTGTTTATTTTTATT    3300
GTTTGCCCCTCTACAGGAGTAAAACTAGGATTCTAGAATTCCGAGCCTCAAGTCAATGCTGTGAAGCCTCCTACTTCCTGTTACCTCACCTTTTGTAGCA    3400
TTGCACTTGTTCAAAGGATGCTGTAGCGCCCAATGCCTGCCACAGGCTTGTACAGTGTCTGTTTACTGTGACTCAATGGATTTATTTTTGGAGCTTTTC    3500
AATATGACTTAAAGCAAAAGAAATTCATACGGGTGGGTAAATAATTCAAAGAACTAAAAGGGACTTGGAAATGAATACATAAGACTCCAGAAGAGTACA    3600
ATTGCAGCTCATTTGAGAGATAGGCTTTGTTCATGTTGAAGTCATGTTTCTAGTAAACACTAATTTTAATGCTATCCTTGAGGTTTCTTATAGACATTT    3700
TTTTTTTTTTTTTTTTGGAGCTGGGGACTGAACCCAGGGCAAGCGCTCTACGCTGAGCTAAATCCCCAACCCCTTATAGAGAATTTCAGCAATCACAT    3800
TCACAAATAAAATGGGATTCTAGTTACTAAGTCAATCAAGATTATATGTATCATTTGTTAGAAATAAGTTAATTTAAAAATATTAGTTTATAGTCAATTG    3900
CCTAGGTTCTTCTGATGCTGAGGTTTAAAAAAACAAAACAAAAAAAGATTTCACTTTGAAACCTGGGAATATTATTATTTCTAACATGTGTTTGTGTCGT    4000
TCATCCTAGTACAGTTCATTTAAGTGACTTTATTTCCTCTTCTCATGATTTTAGTTGGAAGAGGCTGGCTGGGTAGGGTAGACGGAACTGGATGTTTTTAG    4100
TTGCTTAAATAATTATTGTCATGAAGTATATAATGCAAAACTATTTATGTTTTGAATGAATTGGTCATATCACCAATAAAATCAGTTGTTGAGAAACCA    4200
AAAAAAAAA
```

FIG. 3B

```
B
DH1 (Rat)    MLRNLFRRRL  FSYPTKYYFM  VLVLSLITFE  VVRIHQKPEF  VSVSHLELBG  DDPNSNVNCT   60
Mouse        ----------  ------C---  --------L-  -----L----  F--R----A-  -----Y----
Human        ----------  ----------  ----------  -----L----  -------A--  EN-S-DI---

DH1 (Rat)    KVLQGDPEEI  QKVKLEILTV  QEKKRPRRTP  HEYTNMTRDC  ASFIRTRKYI  MEPLTKEEVG  120
Mouse        --I-------  ----------  -------W--  ----------  ----------  V---------
Human        ----------  ----------  -KF----W--  DD-I----S-  S----KR---  V----S--AE DH1 (Rat)    FPIAYSIVVH  HKIDMLDRLL  RAIYMPQNFY  CIHVDRKAEE  SFLAAVQGIA  SCFDNVFVAS  180
Mouse        ----------  ----E-----  ----------  ----------  ----------  ----------
Human        ----------  ----E-----  ----------  --V--T-S-D  --Y----M--  -------S--

DH1 (Rat)    QLESVVYASW  SRVKADLNCM  KDLYRMNANW  KYLNLCGMD  FPIKTNLEIV  RKLFSFTGEN  240
Mouse        ----------  T---------  ----------  ----------  ----------  -------CS-
Human        R---------  ----Q-----  -----A----  ----------  ----------  ------LLM- DH1 (Rat)    SLETEKMPPN  KEKRWKYRY  VVDGKLTNTG  VVKAQPPLKT  PLFSGSAYFV  VTREYVGYVL  300
Mouse        ----------  T---------  ----------  ----------  ----------  ----------
Human        N---------  ----------  ----------  ----------  ----------  -------S--

DH1 (Rat)                                       I---------
Mouse        N-------A-  ----------  -----N----  T--ML---E-
Human        N-------E-

DH1 (Rat)    ENKNIQKFME  WAQDTYSPDE  FLWATIQRIP  EVPGSLPSSH  KYDLSDMNAV  ARFVKWQIFE  360
Mouse        --E----L--  ----------  ----------  ----F--N--  --------I-  ----------
Human        Q-EK----L-  ----------  ----F-----  -------A--  ------Q---  ----------

DH1 (Rat)    GDVSNGAPYP  PCSGVHVRSV  CVFGVGDLSW  MLRKHHFFAN  KFDMDVDPFA  LQCLEEHLRH  420
Mouse        ----------  ----D-----  ----A-----  ----Q--L--  ----------  I----D---R
Human        -----K----  ----------  ----I-A--N- -------L--  ----VT--L-  I----D----

DH1 (Rat)    KALETLER                                                                428
Mouse        -----N--H
Human        -----KH
```

FIGURE 9

```
LOCUS       HUMC2CNT    2204 bp    DNA         PRI      10-APR-1996
DEFINITION  Homo sapiens core 2 beta-1,6-N-acetylglucosaminyltransferase (core
            2 GnT) gene, complete cds.
ACCESSION   L41415
NID         g886272
KEYWORDS    beta-1,6-N-acetylglucosaminyltransferase.
SOURCE      human.
  ORGANISM  Homo sapiens
            Eukaryotae; mitochondrial eukaryotes; Metazoa; Chordata;
            Vertebrata; Eutheria; Primates; Catarrhini; Hominidae; Homo.
REFERENCE   1  (bases 1 to 2204)
  AUTHORS   Bierhuizen,M.F., Maemura,K., Kudo,S. and Fukuda,M.
  TITLE     Genomic organization of core 2 and I branching
            beta-1,6-N-acetylglucosaminyltransferases. Implication for
            evolution of the beta-1,6-N-acetylglucosaminyltransferase gene
            family
  JOURNAL   Glycobiology 5 (4), 417-425 (1995)
  MEDLINE   96078409
FEATURES             Location/Qualifiers
     source          1..2204
                     /organism="Homo sapiens"
                     /note="(vector lambda EMBL3)"
                     /map="chromosome 9"
                     /tissue_type="placenta"
     intron          <1..100
                     /number=1
     exon            101..2204
                     /number=2
                     /codon_start=1
     CDS             244..1530
                     /gene="core 2 GnT"
                     /EC_number="2.4.1.102"
                     /note="core 2"
                     /codon_start=1
                     /product="beta-1,6-N-acetylglucosaminyltransferase"
                     /db_xref="PID:g886273"
                     /translation="MLRTLLRRRLFSYPTKYYFMVLVLSLITFSVLRIHQKPEFVSVR
                     HLELAGENPSSDINCTKVLQGDVNEIQKVKLEILTVKFKKRPRWTPDDYINMTSDCSS
                     FIKRRKYITVEPLSKEEAEFPIAYSIVVHHKIEMLDRLLRAIYMPQNFYCVHVDTKSED
                     SYLAAVMGIASCFSNVFVASRLESVVYASWSRVQADLNCMKDLYAMSANWKYLINLCG
                     MDFPIKTNLEIVRKLKLLMGENNLETERMPSHKEERWKKRYEVVNGKLTNTGTVKMLP
                     PLETPLFSGSAYFVVSREYVGYVLQNEKIQKLMEWAQDTYSPDEYLWATIQRIPEVPG
                     SLPASHKYDLSDMQAVARFVKWQYFEGDVSKGAPYPPCDGVHVRSVCIFGAGDLNWML
                     RKHHLFANKFDVDVDLFAIQCLDEHLRHKALETLKH"
BASE COUNT      641 a    414 c    498 g    651 t
ORIGIN
        1 gatttattgt gaaaaactct ctctctctct ctctctctgt atatatatat atatatatat
       61 atatatttat ttatatttat aattgcttct tttatttcag tgctgctctt catttcaaga
      121 tgccgttgca gctctgataa atgcaaactg acaaccttca aggccacgac ggagggaaaa
      181 tcattggtgc ttggagcata gaagactgcc cttcacaaag gaaatccctg attattgttt
      241 gaaatgctga ggacgttgct gcgaaggaga ctttttcttt atcccaccaa atactacttt
      301 atggttcttg ttttatccct aatcaccttc tccgtttaa ggattcatca aaagcctgaa
      361 tttgtaagtg tcagacactt ggagcttgct ggggagaatc ctagtagtga tattaattgc
      421 accaaagttt tacagggtga tgtaaatgaa atccaaaagg taaagcttga gatcctaaca
      481 gtgaaattta aaaagcgccc tcggtggaca cctgacgact atataaacat gaccagtgac
      541 tgttcttctt tcatcaagag acgcaaaatat attgtagaac cccttagtaa agaagaggcg
      601 gagtttccaa tagcatattc tatatggtt catcacaaga ttgaaatgct tgacaggctg
      661 ctgagggcca tctatatgcc tcagaatttc tattgcgttc atgtggacac aaaatccgag
      721 gattcctatt tagctgcagt gatgggcatc gcttcctgtt ttagtaatgt ctttgtggcc
```

FIGURE 9 (cont'd)

```
 781 agccgattgg agagtgtggt ttatgcatcg tggagccggg ttcaggctga cctcaactgc
 841 atgaaggatc tctatgcaat gagtgcaaac tggaagtact tgataaatct ttgtggtatg
 901 gattttccca ttaaaaccaa cctagaaatt gtcaggaagc tcaagttgtt aatgggagaa
 961 aacaacctgg aaacggagag gatgccatcc cataaagaag aaaggtggaa gaagcggtat
1021 gaggtcgtta atggaaagct gacaaacaca gggactgtca aaatgcttcc tccactcgaa
1081 acacctctct tttctggcag tgcctacttc gtggtcagta gggagtatgt ggggtatgta
1141 ctacagaatg aaaaaatcca aaagttgatg gagtgggcac aagacacata cagccctgat
1201 gagtatctct gggccaccat ccaaaggatt cctgaagtcc cgggctcact ccctgccagc
1261 cataagtatg atctatctga catgcaagca gttgccaggt ttgtcaagtg gcagtacttt
1321 gagggtgatg tttccaaggg tgctccctac ccgccctgcg atggagtcca tgtgcgctca
1381 gtgtgcattt tcggagctgg tgacttgaac tggatgctgc gcaaacacca cttgtttgcc
1441 aataagtttg acgtggatgt tgacctcttt gccatccagt gtttggatga gcatttgaga
1501 cacaaagctt tggagacatt aaaacactga ccattacggg caattttatg aacaagaaga
1561 aggatacaca aaacgtaccc ttatctgttt cccttcctt gtcagcatcg ggaagatggt
1621 atgaagtcct ctttggggca gggactctag tagatcttct tgtcagagaa gctgcatggt
1681 ttctgcagag cacagttagc tagaaaggtg atagcattaa atgttcatct agagttaata
1741 gtgggaggag taaaggtagc cttgaggcca gagcaggtag caaggcattg tggaaagagg
1801 ggaccagggt ggctggggaa gaggccgatg cataaagtca gcctgttcaa agtgctcagg
1861 gacttagcaa aatgagaaga tgtgacctgt gccaaaacta ttttgagaat tttaaatgtg
1921 accatttttc tggtatgaat aaacttacag caacaaataa tcaaagatac aattaatctg
1981 atattatatt tgttgaaata gaatttgat tgtactataa atgattttgt taaataattt
2041 atattctgct ctaatactgt actgtgtagt gtgtctccgt atgtcatctc agggagctta
2101 aaatgggctt gatttaacat tgttttttgtg ttattttttgc ttgaaacaac gcacacattt
2161 tcaacaacca aaaaatgaca atttctagtt tagttaattt ctac
```

INHIBITORS OF UDP-G1CNAC:GA1β1-3GA1NACαR β1-6 N-ACETYLGLUCOSAMINYLTRANSFERASE (CORE 2 G1CNAC-T) AND USE OF THE INHIBITORS TO PREVENT OR TREAT CARDIOMYOPATHY ASSOCIATED WITH DIABETES

CROSS REFERENCE TO RELATED APPLICATIONS

This application claims benefit of provisional application 60/046,876 filed Oct. 2, 1996 now abandoned.

FIELD OF THE INVENTION

The invention relates to methods for preventing or treating cardiomyopathy associated with diabetes mellitus and hyperglycemia by inhibiting UDP-GlcNAc:Galβ1-3GalNAcαR β1-6 N-acetylglucosaminyltransferase (core 2 GlcNAc-T); methods for screening for substances that affect cardiomyopathy associated with diabetes mellitus and hyperglycemia; and methods and pharmaceutical compositions containing the substances for preventing or treating cardiomyopathy associated with diabetes mellitus and hyperglycemia.

BACKGROUND OF THE INVENTION

Cardiovascular diseases are the major cause of morbidity and mortality in diabetic patients, involving cardiac tissues as well as large vessels in the brain, heart, and lower extremities (1). In the heart, the majority of the cardiac failure is probably due to atherosclerotic processes in the coronary vessels, but multiple studies have documented that a sizeable number of diabetic patients suffer from congestive heart failure without significant coronary disease (2, 3). In addition, type I diabetic patients with <5 yr of disease have been reported to have abnormal cardiac function in the absence of significant coronary vessel disease (4). These clinical findings are supported further by animal studies documenting biochemical and functional changes in the cardiac tissue shortly after induction of diabetes (5–8). From these results, it has been postulated that diabetes mellitus and its metabolic sequelae can induce a specific form of cardiomyopathy (8, 9).

As with other chronic complications of diabetes, the cardio-vascular changes once established are difficult to reverse, both in clinical and experimental settings (10–12). Most cardiovascular abnormalities are metabolically induced with a great deal of interest directed towards identifying alterations in gene expression induced by diabetes or hyperglycemia in the vasculature. Since thickening of basement membrane is a classical finding in diabetes microvasculature (10), many of the studies concerning glucose-regulated genes have primarily focused on changes in the basement matrix components using cultured vascular cells (13, 14).

SUMMARY OF THE INVENTION

The present inventors have shown a direct association between UDP-GlcNAc:Galβ1-3GalNAcαR β1-6 N-acetylglucosaminyltransferase (core 2 GlcNAc-T) and diabetic cardiovascular disease. In particular, core 2 GlcNAc-T activity was increased by 82% in diabetic hearts versus controls, while the enzymes GlcNAc-T1 and GlcNAc-TV responsible for N-linked glycosylation were unchanged. The results indicate that core 2 GlcNAc-T is specifically induced in the heart by diabetes or hyperglycemia.

Significantly, increased core 2 GlcNAc-T activity caused pathology in the heart of diabetic experimental animal models which is similar to that observed in the heart of diabetic patients after years with the condition. In particular, a transgenic mouse was made with core 2 GlcNAc-T expression driven by a cardiac myosin promoter. At 4 months, a marked hypertrophy of the left ventricle and general hypertrophy of the heart was observed.

The findings by the present inventors indicate that inhibiting core 2 GlcNAc-T can be useful in preventing or treating cardiomyopathy associated with diabetes and hyperglycemia. It also permits the identification of substances which affect core 2 GlcNAc-T and which may be used in the prevention and treatment of cardiomyopathy associated with diabetes and hyperglycemia.

Therefore, broadly stated the present invention relates to a method of preventing or treating cardiomyopathy associated with diabetes and hyperglycemia in a subject comprising reducing core 2 GlcNAc-T activity. Levels of core 2 GlcNAc-T activity may be reduced by administering a substance which inhibits core 2 GlcNAc-T activity. Substances which inhibit core 2 GlcNAc-T activity include known inhibitors of core 2 GlcNAc-T activity, inhibitors identified using the methods described herein, and antisense sequences of a nucleic acid sequence encoding core 2 GlcNAc-T activity.

The invention also relates to a method for screening for a substance that may be used to prevent or treat cardiomyopathy associated with diabetes and hyperglycemia. In an embodiment of the invention, a method of screening for a substance for use in preventing or treating cardiomyopathy associated with diabetes and hyperglycemia is provided comprising assaying for a substance that inhibits core 2 GlcNAc-T activity. A substance that inhibits core 2 GlcNAc-T activity may be identified by reacting core 2 GlcNAc-T with an acceptor substrate and a sugar nucleotide donor in the presence of a substance suspected of inhibiting core 2 GlcNAc-T, under conditions whereby the core 2 GlcNAc-T produces a reaction product, determining the amount of reaction product, and comparing the amount of reaction product to an amount obtained for a control in the absence of the substance, wherein lower amounts of reaction product with the substance indicate that the substance inhibits core 2 GlcNAc-T.

Substances which inhibit core 2 GlcNAc-T may also be identified using the methods of the invention by comparing the pattern and level of expression of core 2 GlcNAc-T in tissues and cells in the presence, and in the absence of the substance.

Substances which inhibit core 2 GlcNAc-T may also be assayed by treating a cell which expresses core 2 GlcNAc-T with a substance which is suspected of inhibiting core 2 GlcNAc-T activity, and assaying for Galβ1-3[GlcNAcβ1-6]GalNAcα- associated with the cell.

Substances which inhibit transcription or translation of the gene encoding core 2 GlcNAc-T may be identified by transfecting a cell with an expression vector comprising a recombinant molecule containing a nucleic acid sequence encoding core 2 GlcNAc-T, the necessary elements for the transcription and/or translation of the nucleic acid sequence and a reporter gene, in the presence of a substance suspected of inhibiting transcription or translation of the gene encoding core 2 GlcNAc-T activity, and comparing the level of expression of core 2 GlcNAc-T or the expression of the protein encoded by the reporter gene with a control cell transfected with the nucleic acid molecule in the absence of the substance. The method can be used to identify transcription and translation inhibitors of the gene encoding core 2 GlcNAc-T.

The substances identified using the method of the invention may be used to prevent or treat cardiomyopathy associated with diabetes and hyperglycemia. Accordingly, the substances may be formulated into pharmaceutical compositions for adminstration to individuals suffering from this condition.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIG. 3 shows the nucleotide and deduced amino acid sequence of DH1 identifying the sequence as core 2 GlcNAc-T;

FIG. 9 shows the nucleotide and amino acid sequence of human core 2 GlcNAc-T.

DETAILED DESCRIPTION OF THE INVENTION

Figure 1A:
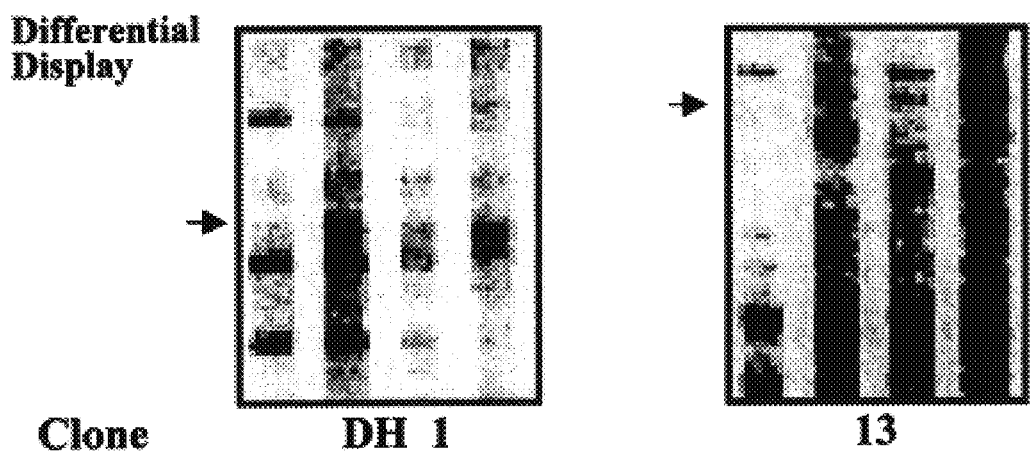
FIG. 1 are blots of differential expressed cDNA fragments (A) and Northern blot analysis (B and C) showing differential expression in control (C) and diabetic heart (D) of the cDNA fragments identified in Panel A.

As discussed above, the present invention relates to a method of preventing or treating cardiomyopathy associated with diabetes and hyperglycemia comprising reducing core 2 GlcNAc-T activity. Levels of core 2 GlcNAc-T activity may be reduced by administering a substance which inhibits core 2 GlcNAc-T activity, or inhibits transcription or translation of the gene encoding core 2 GlcNAc-T.

Substances which inhibit core 2 GlcNAc-T activity include known inhibitors of core 2 GlcNAc-T. Examples of inhibitors of core 2 GlcNAc-T include an analog of the acceptor substrate for core 2 GlcNAc-T such as Gal$\beta$1-3GalNAc$\alpha$. Inhibitors of enzymes earlier on in the Golgi oligosaccharide processing pathway may also be used to inhibit core 2 GlcNAc-T derived product, for example UDP-Gal:GalNAc$\alpha$R$\beta$1-3 galactosyltransferase or UDP-GalNAc:Ser/thr $\alpha$N-acetylgalactosyltransferase.

Recombinant molecules containing the nucleic acid sequence of core 2 GlcNAc-T in antisense orientation may be used to inhibit core 2 GlcNAc-T activity. The nucleic acid sequence shown in FIG. 9 (see also GenBank Accession Nos. L41415, U41320, and U19265), or parts thereof, may be inverted relative to their normal presentation for transcription to produce antisense nucleic acid molecules. The antisense nucleic acid molecules may be contructed using chemical synthesis and enzymatic ligation reactions using procedures known in the art. The antisense nucleic acid molecules or a part thereof, may be chemically synthesized using naturally occurring nucleotides or variously modified nucleotides designed to increase the biological stability of the molecules, or to increase the physical stability of the duplex formed with mRNA or the native gene e.g. phosphorothiate derivatives and acridine substituted nucleotides. The antisense sequences may be produced biologically using an expression vector introduced into cells in the form of a recombinant plasmid, phagemid, or attenuated virus in which antisense sequences are produced under the control of a high efficiency regulatory region, the activity of which may be determined by the cell type into which the vector is introduced.

The invention also provides methods for screening for a substance that may be used to prevent or treat cardiomyopathy associated with diabetes and hyperglycemia. In an embodiment of the invention, a method of screening for a substance for use in preventing or treating cardiomyopathy associated with diabetes and hyperglycemia is provided comprising assaying for a substance that inhibits core 2 GlcNAc-T activity. A substance that inhibits core 2 GlcNAc-T activity may be identified by reacting core 2 GlcNAc-T with an acceptor substrate and a sugar nucleotide donor in the presence of a substance suspected of inhibiting core 2 GlcNAc-T, under conditions whereby the core 2 GlcNAc-T transfers the sugar nucleotide donor to the acceptor substrate to produce a reaction product, determining the amount of reaction product, and comparing the amount of reaction product to an amount obtained for a control in the absence of the substance, wherein lower amounts of reaction product with the substance indicate that the substance inhibits core 2 GlcNAc-T.

The acceptor substrate may be an oligosaccharide, a glycopeptide, or a glycoprotein having the following minimal structure for the oligosaccharide portion Gal$\beta$1-3GalNAc$\alpha$-R where R is any convenient group $\alpha$ linked covalently to the 1 position of the GalNAc residue of the acceptor, for example p-nitrophenol, or octyl. The sugar nucleotide donor is uridine diphospho-N-acetylglucosamine (UDP-GlcNAc) which can be labelled in the GlcNAc portion with radioactive groups or other nonradioactive groups which can be used for product detection. The concentration of the acceptor substrate and of the labelled UDP-GlcNAc in the reaction may range from 0.01 mM to 10 mM and the duration of the reaction from 5 minutes to 24 hours.

Conditions are selected so that the core 2 GlcNAc-T transfers the sugar nucleotide donor to the acceptor substrate to produce a reaction product. The substrate and sugar donor are effective to interact with the core 2 GlcNAc-T within wide pH and temperature ranges, for example from about 5 to 8 and from about 30 to 45° C., preferably from 37° C.

The core 2 GlcNAc-T may be obtained from commercial sources, or prepared by expression of the gene encoding core 2 GlcNAc-T in host cells (for example, transfected CHO cells). A substance that inhibits core 2 GlcNAc-T activity may also be identified by treating a cell which expresses core 2 GlcNAc-T with a substance which is suspected of affecting core 2 GlcNAc-T activity, and assaying for Galβ1-3 [GalNAcβ1-6]GalNAcα associated with the cell. Galβ1-3 [GalNAcβ1-6]GalNAcα can be measured using a substance that binds to the oligosaccharide product either alone or in association with an attached glycoprotein. For example, cells expressing core 2 GlcNAc-T may be treated with a substance suspected of inhibiting core 2 GlcNAc-T activity. An antibody specific for the oligosaccharide product can be added and the amount of antibody binding can be compared to control cells which have not been treated with the substance and/or which do not express core 2 GlcNAc-T. Antibodies specific for core 2 GlcNAc-T may be obtained from commercial sources, for example 1B11 rat anti-mouse CD43 activation-associated isoform monoclonal antibody supplied by Pharmingen Inc.

Substances which inhibit core 2 GlcNAc-T include substances which inhibit transcription or translation of the gene encoding core 2 GlcNAc-T. Transcription inhibitors may be identified by transfecting a host cell with a recombinant molecule comprising a nucleic acid sequence encoding core 2 GlcNAc-T, the necessary elements for the transcription of the nucleic acid sequence, and a reporter gene, in the presence of a substance suspected of inhibiting transcription of the gene encoding core 2 GlcNAc-T, and comparing the level of mRNA or expression of the protein encoded by the reporter gene with a control cell transfected with the nucleic acid molecule in the absence of the substance. Translation inhibitors may be identified by transfecting a host cell with a recombinant molecule comprising a nucleic acid sequence encoding core 2 GlcNAc-T, the necessary elements for the transcription and translation of the nucleic acid sequence, and a reporter gene, in the presence of a substance suspected of inhibiting translation of the gene encoding core 2 GlcNAc-T, and comparing the level of expression of core 2 GlcNAc-T with a control cell transfected with the nucleic acid molecule in the absence of the substance.

A recombinant molecule comprising a nucleic acid sequence encoding core 2 GlcNAc-T may be constructed having regard to the sequence of the core 2 GlcNAc-T gene (see FIG. 9) using chemical synthesis and enzymatic ligation reactions following procedures known in the art.

Suitable transcription and translation elements may be derived from a variety of sources, including bacterial, fungal, viral, mammalian, or insect genes. Selection of appropriate transcription and translation elements is dependent on the host cell chosen, and may be readily accomplished by one of ordinary skill in the art. Examples of such elements include: a transcriptional promoter and enhancer, an RNA polymerase binding sequence, a ribosomal binding sequence, including a translation initiation signal. Additionally, depending on the host cell chosen and the vector employed, other genetic elements, such as an origin of replication, additional DNA restriction sites, enhancers, and sequences conferring inducibility of transcription may be incorporated into the expression vector. It will also be appreciated that the necessary transcription and translation elements may be supplied by the native gene and/or its flanking sequences.

Examples of reporter genes are genes encoding a protein such as β-galactosidase (e.g. lac Z), chloramphenicol, acetyl-transferase, firefly luciferase, or an immunoglobulin or portion thereof such as the Fc portion of an immunoglobulin preferably IgG. Transcription of the reporter gene is monitored by changes in the concentration of the reporter protein such as β-galactosidase, chloramphenicol acetyltransferase, or firefly luciferase. This makes it possible to visualize and assay for expression of recombinant molecules to determine the effect of a substance on expression of the core 2 GlcNAc-T gene.

Mammalian cells suitable for carrying out the present invention include, for example, COS (e.g., ATCC No. CRL 1650 or 1651), BHK (e.g., ATCC No. CRL 6281), CHO (ATCC No. CCL 61), HeLa (e.g., ATCC No. CCL 2), and 293 (ATCC No. 1573). Suitable expression vectors for directing expression in mammalian cells generally include a promoter. Common promoters include SV40, MMTV, metallothionein-1, adenovirus Ela, CMV, immediate early, immunoglobulin heavy chain promoter and enhancer, and RSV-LTR.

Protocols for the transfection of mammalian cells are well known in the art and include calcium phosphate mediated electroporation, retroviral, and protoplast fusion-mediated transfection (see Sambrook et al., Molecular Cloning A Laboratory Manual, 2nd edition, Cold Spring Harbor Laboratory Press, 1989).

The reagents suitable for applying the methods of the invention to identify substances that may be used to prevent or treat cardiomyopathy associated with diabetes and hyperglycemia may be packaged into convenient kits providing the necessary materials packaged into suitable containers. The kits may also include suitable supports useful in performing the methods of the invention.

Substances which inhibit core 2 GlcNAc-T activity may be incorporated into pharmaceutical compositions. Therefore, the invention also relates to a pharmaceutical composition comprising an inhibitor of core 2 GlcNAc-T activity and in particular a substance identified using the methods described herein. The pharmaceutical compositions of the invention contain the substance, alone or together with other active substances.

The substances identified using the method of the invention may be formulated into pharmaceutical compositions for adminstration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans, and animals. Administration of a therapeutically active amount of the pharmaceutical compositions of the present invention is defined as an amount effective, at dosages and for periods of time necessary to achieve the desired result. For example, a therapeutically active amount of a substance may vary according to factors such as the disease state, age, sex, and weight of the individual. Dosage regima may be adjusted to provide the optimum therapeutic response. For example, several divided doses may be administered daily or the dose may be proportionally reduced as indicated by the exigencies of the therapeutic situation.

The active substance may be administered in a convenient manner such as by injection (subcutaneous, intravenous, etc.), oral administration, inhalation, transdermal application, or rectal administration. Depending on the route of administration, the active substance may be coated in a material to protect the compound from the action of enzymes, acids and other natural conditions which may inactivate the compound.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

Recombinant molecules comprising an antisense sequence may be directly introduced into cells or tissues in vivo using delivery vehicles such as retroviral vectors, adenoviral vectors and DNA virus vectors. They may also be introduced into cells in vivo using physical techniques such as microinjection and electroporation or chemical methods such as coprecipitation and incorporation of DNA into liposomes. Recombinant molecules may also be delivered in the form of an aerosol or by lavage. Recombinant molecules comprising an antisense sequence may also be applied extracellularly such as by direct injection into cells.

Inhibitors of core 2 GlcNAc-T and pharmaceutical compositions containing the inhibitors have pharmaceutical utility in the prevention and treatment of cardiomyopathy associated with diabetes mellitus and hyperglycemia. The utility of the inhibitors of core 2 GlcNAc-T and compositions of the invention may be confirmed in animal experimental model systems.

The present invention also contemplates a transgenic non-human animal all of whose germ cells and somatic cells contain a DNA construct introduced into the animal, or an ancestor of the animal at an embryonic stage, the DNA construct when incorporated into the germ line of the animal being adapted to develop cardiomyopathy similar to that associated with diabetes mellitus and hyperglycemia. The transgenic animal of the invention is therefore highly suited for investigating the molecular and cellular events involved in cardiomyopathy associated with diabetes mellitus and hyperglycemia, and for in vivo testing of the efficacy of drugs in the prevention or treatment of cardiomyopathy associated with diabetes mellitus and hyperglycemia.

In accordance with one embodiment of the invention, the transgenic non-human animal contains a DNA construct comprising a gene encoding core 2 GlcNAc-T. In accordance with a preferred embodiment of the invention, the transgenic non-human animal contains a DNA construct comprising a gene encoding core 2 GlcNAc-T and a promoter which stimulates expression of the gene in the cardiovascular system. Suitable promoters include the cardiac myosin promoter.

The animals of the invention may be used to test substances for their efficacy in preventing or treating cardiomyopathy associated with diabetes mellitus and hyperglycemia. When an animal is treated with the substance to be tested and a reduced incidence of cardiomyopathy compared to untreated animals is observed, it is an indication of the efficacy of the substance in the prevention or treatment of cardiomyopathy associated with diabetes mellitus and hyperglycemia.

The following non-limiting examples are illustrative of the present invention:

EXAMPLES

Example 1

The following materials and methods were used in the Example:

Animals. Male Sprague-Dawley rats (Taconic Farms, Inc. German Town, N.Y.) weighing 180–200 grams were injected by the intraperitoneal route with STZ (80 mg/kg of body weight). STZ was dissolved in 20 mM cirate buffer (pH 4.5) immediately before use. Cardiac tissue from spontaneous autoimmune-caused diabetic nonobese diabetic (NOD) mice and their contral littermates were graciously provided by Dr. Masakazu Hattori of the Joslin Diabetes Cancer (Boston, Mass.) (19). Onset of diabetes was determined by the detection of urinary glucose and confirmed by blood glucose levels. Insulin pellets (Linshin, Scarborough, Canada) were implanted subcutaneously 1 wk after STZ injection in four STZ-diabetic rats for another week to normalize blood glucose level. The mean plasma blood glucose level in insulin-treated STZ-diabetic rats was not significantly different from control animals (4.8±0.5 vs 5.6±0.7 mM), while, the mean body weight in the insulin-treated STZ-diabetic rats remained significantly less than control (270±17 vs 326±17 grams respectively, P<0.01) but significantly greater than diabetic rats without insulin treatment (210±33 grams), (P<0.01).

mRNA differential display. Rats were killed 2 wk after onset of diabetes. Cardiac ventricles and thoracic aorta were dissected and washed with ice-cold PBS, immediatley frozen in liquid $N_2$ then crushed into frozen powder. Pieces of aorta from three rats were combined into one sample. Total RNA was extracted using Ultraspec RNA isolation system (Biotecx Laboratories, Houston, Tex.). mRNA differential display was performed as previously reported (17, 18). Briefly, DNA-free RNA was obtained by treatment with DNase I (GIBCO BRL, Grand Island, N.Y.) in the presence of placental RNase inhibitor (GIBCO BRL) for 30 min at 37° C. After phenol/chloroform extraction and ethanol precipitation, two reverse transcriptions were performed for each RNA sample using 0.2 $\mu$g DNA-free total RNA in 1×reverse transcription buffer (PCR buffer) containing 10 mM DTT, 20 $\mu$M each of dGTP, dATP, dTTP, and dCTP, and 1 $\mu$M of either $T_{12}$ NG or $T_{12}$NC oligonucleotide (Midland Certified Reagent Co., Midland, Tex.) where N is three-fold degenerate for G, A, and C. The solution was heated at 65° C. for 5 min and cooled to 37° C., then superscript reverse transcriptase (20 U) (GlBCO BRL) was added for 1 h. PCR was performed in reaction mixtures containing 0.1 vol of reverse transcription reaction mixture, 1×PCR buffer, 2 $\mu$M each of dGTP, dATP, dTTP, and dCTP, 10 $\mu$Ci [ -$^{35}$S ]-dATP, 1 $\mu$M of the respective $T_{12}$NX oligonucleotide, 0.2 $\mu$M of 20 different specific arbitrary 10-mer oligonucleotides (OP-ERON Technologies Inc., Almeda, Calif.) and 10 U of AmpliTaq DNA polymerase (Perkin-Elmer Cetus Corp. Norwalk, Conn.). The PCR reactions were initiated at 95° C. for 1 min, amplified 40 cycles at 94° C. for 45 s, 40° C. for 90 s, 72° C. for 30 s, and finished at 72° C. for 15 min. DNA sequencing stop buffer (U.S. Biochemical, Inc., Cleveland, Ohio) was added to samples which were heated at 80° C. for 2 min before loading on a 6% polyacrylamide sequencing gel (National Diagnostics, Atlanta, Ga.). After electrophorosis, the gels were exposed to XAR-5 film (Eastman Kodak Co., Rochester N.Y.) for 48 h. Bands evident under one glycemic condition and absent in the other were identified and the PCR repeated to confurm the findings.

Band recovery and Northern blot analysis. Bands reproducibly exhibiting significant differences in expression were cut out and DNA was eluted by boiling in 10 mM Tris.HCI and 1 mM EDTA solution for 30 min. After ethanol precipitation, the DNA was reamplified by PCR using appropriate primers and conditions described above except for dNTP concentrations of 20 $\mu$M and no radioisotope. Products were visualized on 2% agarose gels, eluted, and used as probes for Northern blot analysis or subcloned. Total RNA (20–25 $\mu$g) was fractionated by denaturing 1% formaldehyde agarose gel electrophoresis and transferred to Biotrans nylon membrane (ICN, Irvine, Calif.). $^{32}$P-labeled probes prepared by random priming using a commercially available kit (Amersham Corp., Arlington Heights, Ill.) were hybridized to UV crosslinked blots in 0.1 M Pipes, 0.2 M NaPO$_4$, 0.1 M NaCl, 1 mM EDTA, 5% SDS, and 60 $\mu$g/ml salmon sperm DNA at 65° C. and washed in 0.5×SSC, 5% SDS at 65° C. for over 1 h. mRNA expression was quantified using a phosphorImager and standardized volume integration with the accompanying ImageQuant Analyzing Software version 3.3 (Molecular Dynamics, Sunnyvale, Calif.) and loading differences were normalized using 36B4 as standard cDNA probe (17, 18).

DNA sequencing. Samples showing significant changes by Northern blot analysis were subcloned using the TA Cloning Kit (Invitrogen Corp., San Diego, Calif.). After the subcloned inserts were checked by Northern blot analysis, DNA sequencing was performed using commercially available Sequenase version 2.0 kit (U.S. Biochemical, Inc.). Gene database searches were performed at the National Center for Biotechnology Information (NCBI) using the BLAST network service.

Construction of the diabetic heart cDNA library. Poly(A)+ RNA was isolated from the total cellular RNA extracted from heart of diabetic rats using an oligo-dT cellulose column (Pharmacia LKB Biotechnology Piscataway, N.J.) as previously described (17). cDNA was prepared and ligated into the EcoRI sites of Lambda gt 10 (Stratagene, Inc., La Jolla, Calif.) by standard methods (20). After packaging the DNA, *Escherichia coli* (C600) was infected with the phage and plated on a P150 plate yielding about 5×10$^4$ independent plaque-forming units. Plaques were lifted onto nitrocellulose (Schleicher & Schuell, Inc., Keene, N.H.) and cross-linked to the membrane by ultraviolet light. 20 P150 plates were screened, which provided 1×10$^6$ plaque-forming units for screening.

Screening the cDNA library. A 214-bp cDNA (DH1) probe obtained from differential display was hybridized to the cDNA library by standard methods at 44° C. then washed at 56° C. (21). After screening 1×10$^6$ plaque-forming units, a positive cDNA insert was isolated and subcloned into pBluescript (Stratagene, Inc.). For sequencing, the inserts were restricted using BamH1 and EcoR1 and subcloned into pBluescript.

cDNA cloning of mouse UDP-GlcNAc:Gal$\beta$1-3Gal/NAc-R $\beta$1-6 N-acetylglucosaminyltransferase (core 2 GlcNAc-T). Approximately 2×10$^5$ colonies of a cDNA library preapred in pCDM8 (Invitrogen Corp.) using poly A+RNA from D33W25, a murine lymphoid tumor cell line (22), were screened by colony hybridization (23) to a 864-bp EcoRI-BamH1 subcloned fragment of human core 2 GlcNAc-T isolated by PCR (gift of Dr. A. Datti, Perugia, Italy) corresponding to amino acids 85–372 of the human enzyme. Hybridization was performed overnight at 65° C. in 500 mM sodium phosphate pH 7.2, 7% SDS, 1% BSA, 1 mM. EDTA After rinsing, filters were washed at 65° C. in 100 mM sodium phosphate, 0.1% SDS. After three rounds of hybridization and purification, two clones, designated C2-251 and C2-352, were isolated and gave specific and strongly positive signals on Southern blots hybridized with the probe. The cDNA inserts were subcloned as XhoI fragments into SalI cut pGEM5zf (+) (Promega Corp., Madison, Wis.) and a series of exonuclease III-mung bean nuclease (GIBCO BRL)— nested deletions generated from each end. DNA sequencing was performed using the Autoread sequencing kit and the ALF DNA sequencer according to the manufacturer's instructions (Pharmacia LKB Biotechnology). Some sequences were also generated using internal primers. Data were analyzed and edited using the UWGCG suite.

Transient expression of DH1 in Cos 7 cells. A cDNA insert containing the full open reading frame of DH1 was isolated with XhoI and EcoRV and subcloned into pcDNAI/amp (Invitrogen Corp.). The plasmid was purified by double CsCl ultracentrifugation followed by phenol/chloroform extraction (21), then DNA (0.5 $\mu$g) was transfected into conconfluent Cos 7 cells cultured on P100 dishes using 20 $\mu$g of Lipofectin for 16 h at 37° C. (GIBCO BRL) (24). Cells were harvested 48 h later and used for measurement of core 2 GlcNAC transferase activity.

Preparation of cardiomyocytes. Cardiomyocytes were prepared by collagenase digestion as described before (25). Briefly, hearts were excised and perfused through the aorta with Krebs-Henseleit bicarbonate buffer containing 5.5 mM glucose and 2.5 mM calcium. The perfused medium was switched to the same buffer without calcium to stop contraction, followed by a final perfusion with Krebs-Henseleit buffer containing 50 $\mu$M calcium, 0.1% BSA, 312 U/ml hyaluronidase (Worthington, Freehold, N.J.) and 0.1% collagenese (Worthington). Ventricular tissue was dissociated by shaking in Krebs-Henseleit buffer containing 50 $\mu$M calcium, 0.2% BSA, 312 U/ml hyaluronidase, and 0.1% collagenase. The cells were allowed to settle under gravity and were washed twice in the Krebs-Henseleit buffer containing 100 $\mu$M calcium and 0.5% BSA before resuspension in minimal essential medium containing Earle's salts, 26 mM sodium bicarbonate, 5 mM creatine, 20 mM Hepes, 100 U/ml penicillin G, 100 $\mu$g/ml streptomycin, and 1.8 mM calcium. The cells were seeded onto laminin-coated dishes and maintained in a 37° C. humidified 0.5% air-5% CO$_2$ incubator. All cells were allowed to equilibrate for 2 h then washed and refed with the same media containing 0.24 gram % BSA and cultured for 3 d with the media changed daily. Some cells were cultured in the same media containing either 22 mM glucose or 10$^{-7}$ M insulin for 3 d with daily changes of media.

Measurement of core 2GlcNAc-T activity. Transfected Cos-7 cells were washed in PBS, frozen, thawed, and lysed in 0.9% NaCl, 04.% Triton X-100 at 0° C. PBS-rinsed, fresh frozen rat hearts were rinsed again in PBS and homogenized using a polytron in 0.9% NaCl, 0.4% Triton X-100, 0.1 mM PMSF, 0.1% Trasylol at 0° C. The core 2 GlcNAc transferase reactions contained 50 M 2-(N-morpholino) ethanesulfonic acid (MES) pH 7.0, 1 mM UDP-GlcNAc, 0.5 $\mu$Ci UDP-6[$^3$H]-N-acetylglucosamine (16,000 dpm/nmol, New England Nuclear, Boston, Mass.), 0.1 M GlcNAc, 1 mM of Gal$\beta$1-3GalNAc -pNp (Toronto Research Chemicals, Toronto, Canada) as substrate, and 16 $\mu$l of cell lysate (8–12 mg/ml of protein) for a final volume of 32 $\mu$l (26, 27). The GlcNAc-TV reactions were the same except that Triton X-100 was added to a final concentration of 1%, and 1 mM of GlcNAc$\beta$1-2Man 1-OMan$\beta$1-O(CH$_2$)$_8$COOCH$_3$ (Dr. O. Hindsgaul, University of Alberta, Edmonton, Canada, was used as acceptor (28). The GlcNAcTI reactions were the same as GlcNAc-TV but with the addition of 10 mM MnCl$_2$, and 1 mM Man 1-3 (Man 1-6)Man$\beta$1-O(CH$_2$)$_8$. COOCH$_3$ was used as acceptor (29). Reactions were incubated for either 1 or 2 h at 37° C., then diluted to 5 ml in H$_2$O and applied to a C$_{18}$ Sep-Pak (Millipore Corp., Bedford, Mass.) in H$_2$O, washed with 20 ml H$_2$O. The products were eluted with 5 ml of methanol and radioactivity was counted in a liquid scintillation $\beta$-counter. Endogenous enzymatic activity was measured in the absence of acceptor and subtracted from values determined in the presence of added acceptor.

Statistical analysis. Differences in signal intensity between controls and diabetic animals were expressed as percentage of controls. Because percentages tends to deviate from normal distribution, mean and standard error were calculated after transformation of data to logarithmic values and data were expressed as mean (±SE range). Statistical analysis (Student's t test) was performed using the logarithmic values.

Results

Differenitial display. The expression of mRNA species derived from the cardiac ventricles of diabetic and control rats was compared using mRNA differential display. Approximately 2,000, presumably different, mRNA species were screened in this study using 40 combinations of primer sets. As exemplified by FIG. 1(A), eight candidates appeared differentially expressed when ventricular tissue from control and diabetic rats was compared; five increased and three decreased their expression in the diabetic state. These changes were confirmed by repetition at least twice using different preparations of total RNA.

Figure 1B:
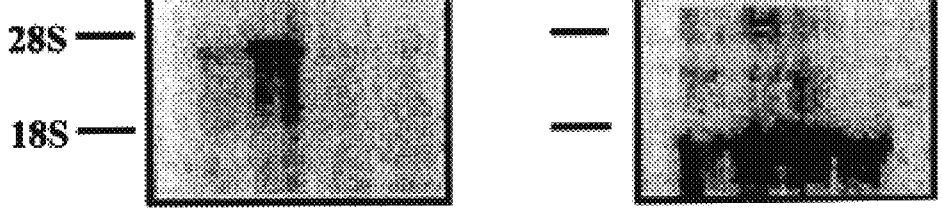
Figure 1C:
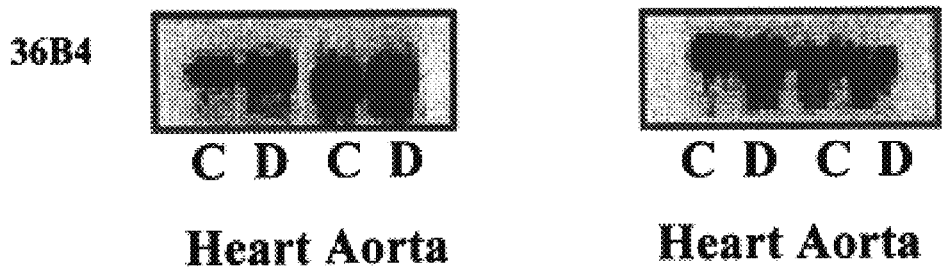
Figure 2:
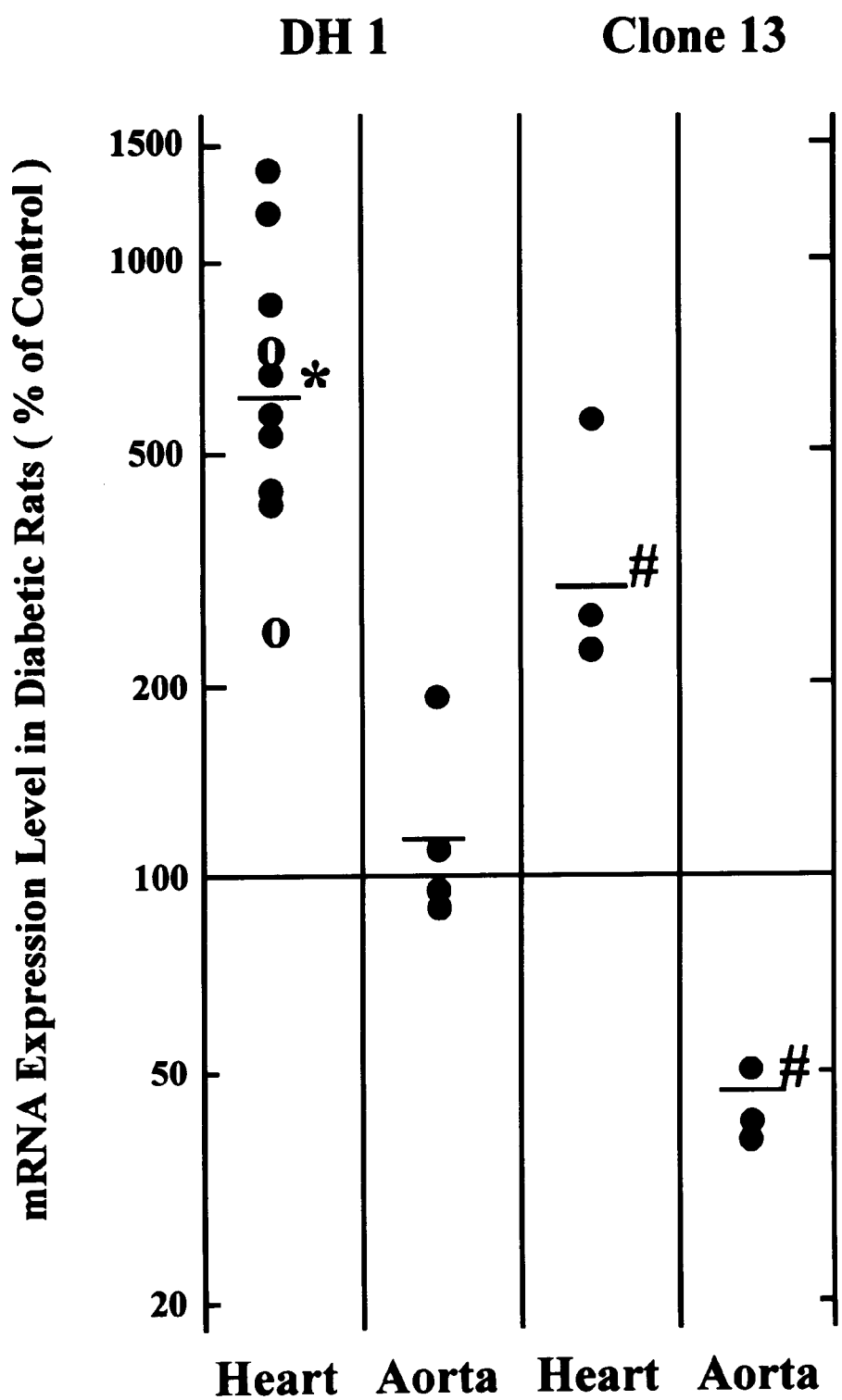
FIG. 2 shows the quantitation of changes induced by diabetes in mRNA levels for DH1 and clone 13 in heart and aorta.

Northern blot analysis. Signals from all the candidates were detectable by Northern blot analysis using total RNA preparations. As shown in FIG. 1(B), two of the eight candidate species showed significant and reproducible changes in diabetic rats compared to controls. FIG. 2 demonstrates that in rats diabetic for 2 wk, the level of DH1 (5.0 kb) increased to 680% (580–790%, n=8, P<0.001) of control in the heart but was not detectable in the aorta. Furthermore, in rats with diabetes for just 1 wk, the mRNA level of DH1 in the heart had already significantly increased to 410% of control levels. A significant increase of DH1 in the heart of diabetic rats was observed even after 4 wk of disease. The expression of clone 13 mRNA increased to 350% (260–470%, n=3, P<0.05) of control in the heart and decreased to 43% (38–49%, n=3, P<0.05) of control in the aorta.

Sequence analysis of DH1 and clone 13. The nucleotide sequences of cDNA fragments of DH1 and clone 13 derived from differential display were determined. Both had flanking primer sequences identical to those used in the differential display. Searching the national gene databases (GenBank/EMBL) revealed that clone 13 had 99% identity to the Wistar rat mitochondrial 16S ribosomal (30) while DH1, which was 214 bp in size, did not reveal any homology to previously reported sequences.

Cloning full-length DH1 cDNA. To facilitate identification, a cDNA library derived from diabetic rat heart mRNA was screened using the 214-bp-cloned DH1 PCR fragment as a probe. Five overlapping recombinants were identified and the composite of the full cDNA sequence was determined (FIG. 3(A)). It contained 5,010 bp inclusive of poly A tail and corresponded to the size detected by the original Northern blot analysis. Open reading frame analysis showed that the longest possible coding region which was from position 802 to 2085 and encoded 428 amino acids. The GXXATGC pattern was observed flanking the region of the presumptive start codon (31) and a polyadenylation signal, AATAAA, was found 15 bp upstream from the polyA tail. Searches for homologous sequences in Genbank/EMBL revealed that this cDNA shared 80% identity at the nucleotide level and 85% identity at the amino acid level with human core 2 (GlcNAc-T) (32). The mouse core 2 GlcNAc-T was also cloned and sequenced and it was found that DH1 shared 92% identity with the amino acid sequence of mouse core 2 GlcNAc-T (FIG. 3(B)). These findings strongly suggested that DH1 was rat core 2 GlcNAc-T.

Figure 4:
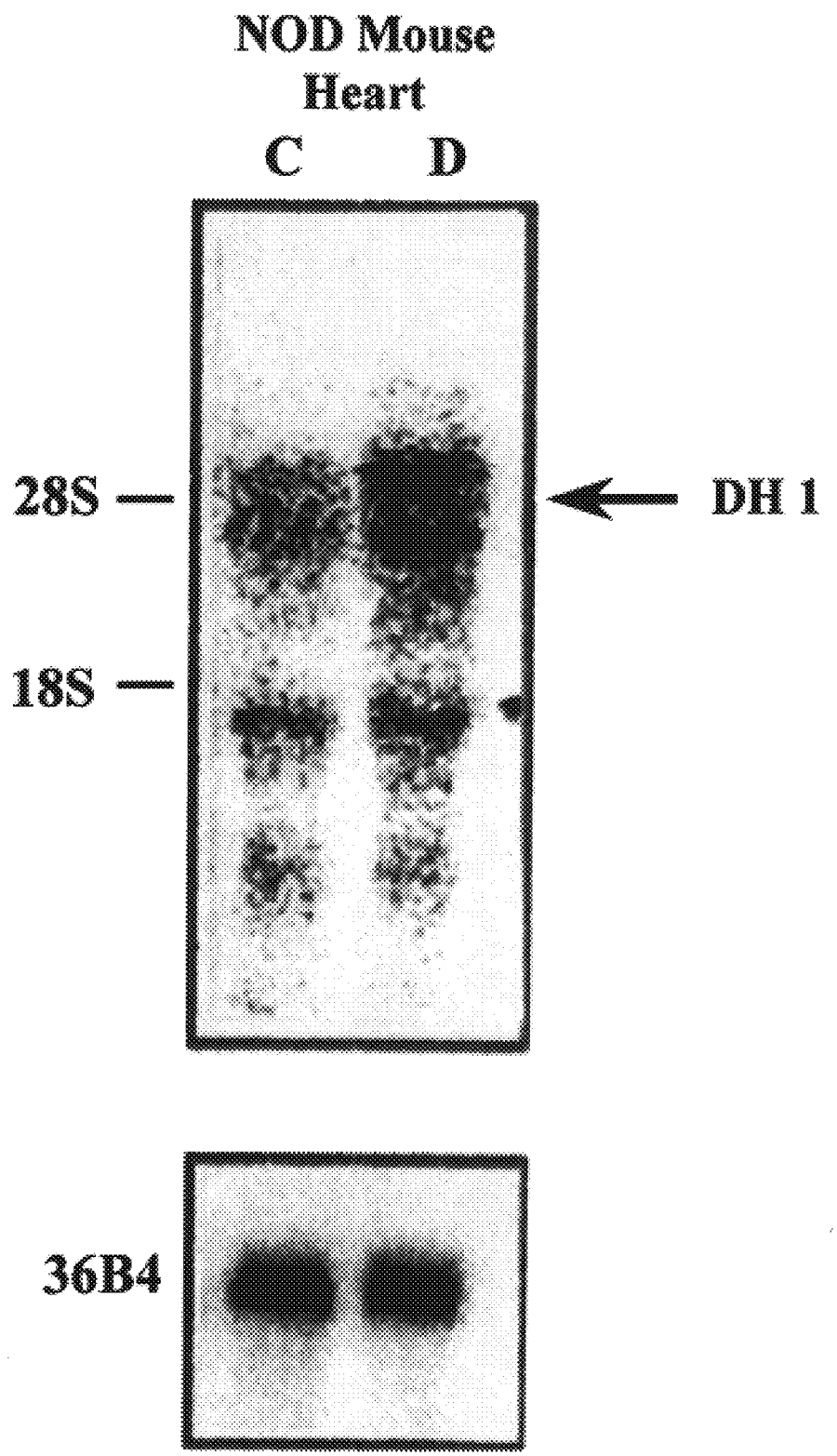
FIG. 4 is a Northern blot analysis for DH1 expression performed using 25 $\mu$g total cellular RNA isolated from age-matched non-obese diabetic (NOD) control mice (C) and diabetic NOD mice (D)

Characterization of DH1 expression in the NOD mouse. To check that increased expression of DH1 was diabetes specific and not due to other effects of streptozotocin, DH1 expression in the hearts of spontaneous autoimmune-caused diabetic NOD mice was measured. As shown in FIG. 4, DH1 hybridizing signals were detected by Northern blot analysis at 6.0, 4.6, and 1.9 kb from animals which had experienced 2–3 wk of hyperglycemia and diabetes. The 4.6 and 6.0 kb bands in hearts from diabetic NOD mice increased to 560% of control animals.

Figure 5:
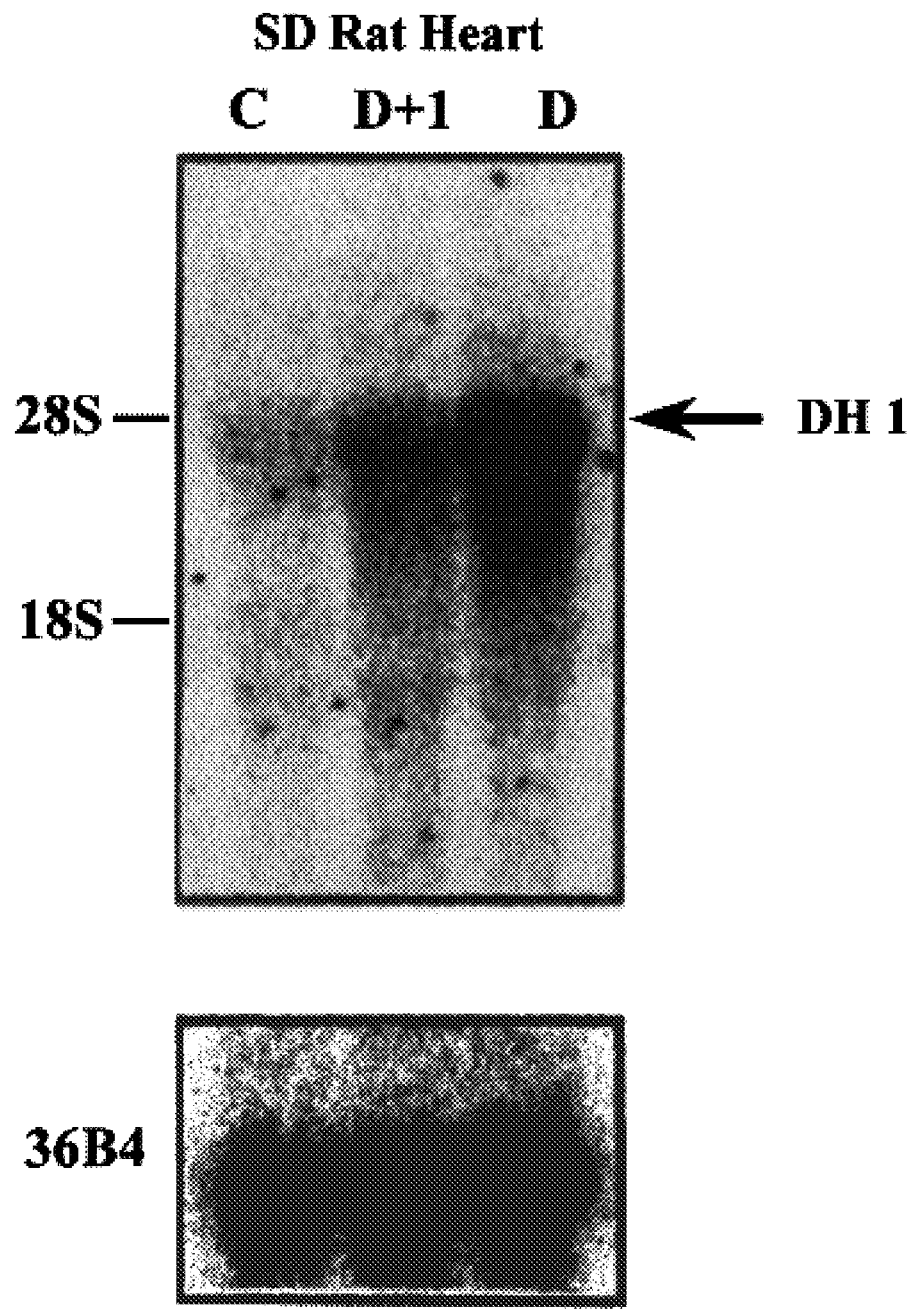
FIG. 5 is a Northern blot analysis for DH1 expression using 25 $\mu$g total cellular RNA isolated from heart of control rat (C) and 2 week diabetic rat without insulin treatment (D) or with insulin treatment for 1 week (D+I)

Effects of insulin on DH1 expression in diabetic rats. After 1 wk of diabetes, four rates were treated with insulin for an additional week. Blood glucose level was normalized from 24.7 to 4.8 mM (P<0.01). The Northern blot analysis shown in FIG. 5, demonstrated that cardiac expression of DH1 in rats diabetic for 2 wk increased to 680% of control levels, consistent with earlier data, whereas insulin treatment normalized the expression of the DH1 to 169% (134–214%P<0.001 vs 2-wk diabetic rats) of control levels.

Figure 6A:
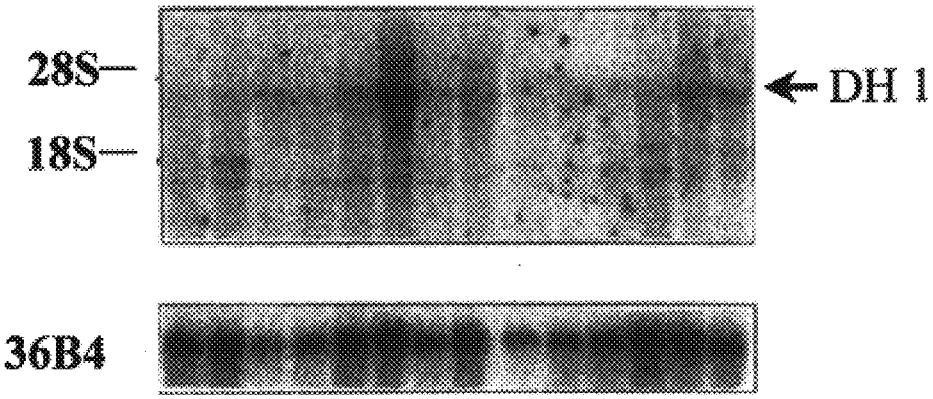
FIG. 6(A) is a Northern blot analysis using 20 $\mu$g total RNA isolated from aorta, brain, heart, kidney, liver, soleus muscle, and lung of control (C) and 2 week diabetic (D) rats, and the same blot reprobed with 36B4 cDNA as a control.
Figure 6B:
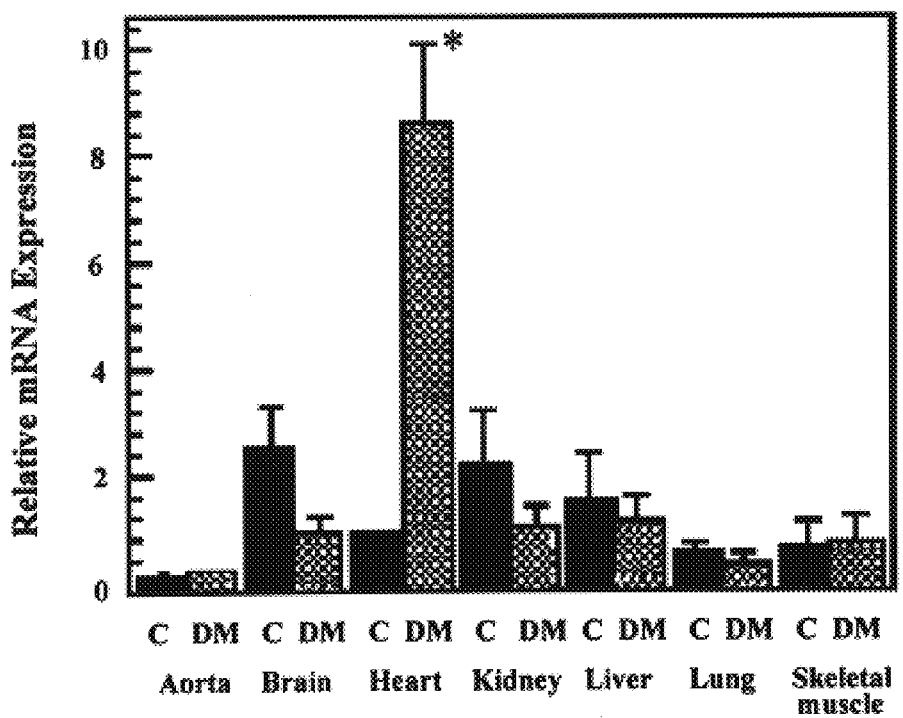
FIG. 6(B) is a bar graph showing the quantitative changes in DH1 levels induced by diabetes in aorta, brain, heart, kidney, liver, lung, and skeletal muscle.

Tissue distribution of DH1. FIG. 6(A) shows a representative Northern blot analysis of DH1 expression using total cellular RNA isolated from tissues of control and diabetic rats. Relative signal intensity was calculated using the 36B4 signal for normalization and is shown in FIG. 6(B). In normal rats, DH1 transcripts were relatively high in the brain kidney and liver and low in the heart aorta, lungs, and skeletal (soleus) muscle. A significant and cardiac specific increase (6.8-fold) in the expression of DH1 mRNA was observed in diabetic animals.

Figure 7A:
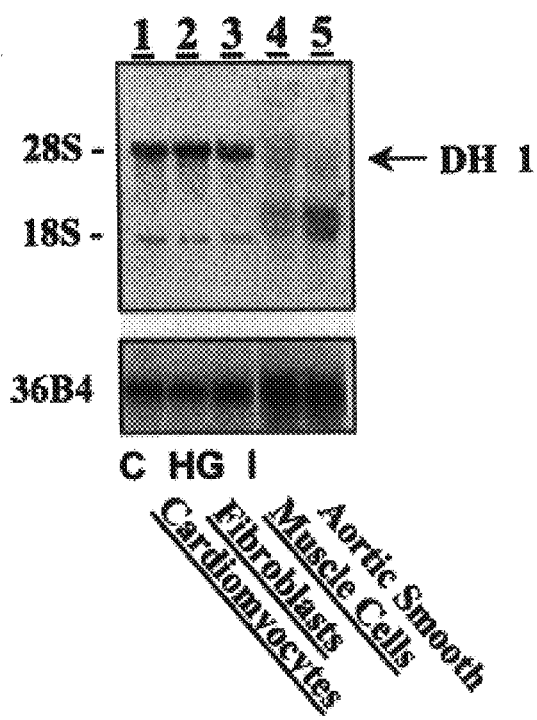
FIG. 7(A) is a blot of total cellular RNA from cultured cardiomyocytes (lanes 1–3), fibroblasts (lane 4),and rat aortic smooth muscle cells (lane 5), probed with DH1.
Figure 7B:
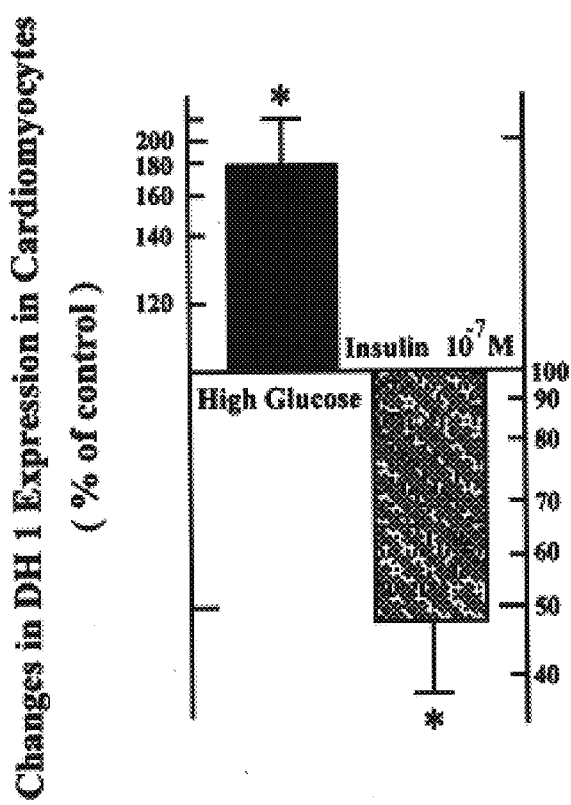
FIG. 7(B) is a graph showing the quantitation of changes induced by 22 mM glucose or 100 nM insulin for DH1 expression in cultured cardiomyocytes.

The expression of DH1 in cultured cells. Cultured cardiomyocytes were measured to determine whether they could be the source of the increased expression of DH1. As shown in FIG. 7(A,) DH1 hybridizing signals were detected by Northern blot analysis of cultured cardiomyocytes at the same mobility as the mRNA from heart tissue (5.0 kb). However, DH1 expression was not detectable in fibroblasts cultured from rat heart or rat aortic smooth muscle cells even when using 25 μg of total cellular RNA. Furthermore, in cardiomyocytes, cultures elevating media glucose concentration from 5.5 to 22 mM increased the expression of the DH1 by 78% (54–106%, P<0.05) while insulin ($10^{-7}$M) decreased the expression by 53% (40–62%, P<0.05) of control levels as shown in FIG. 7(B).

Core 2 GlcNAc-T activity in cells transiently transfected with DH1. Although Cos 7 cells lipofected with pcDNAgI/amp showed significant endogenous core 2 GlcNAc-T activity of 1.71±0.27 nmol/mg per h (g=3), cells transfected with the expression vector containing a full-length cDNA for DH1 in correct orientation had 3.85±1.6 nmol/mg per h (P<0.05, n=3). The assay is specific for core 2 GlcNAc-T, as confirmed by analysis of the reaction product Galβ1-3[GlcNAcβ1-6]-GalNAc pNp by 1 H-NMR (Nuclear Magnetic Resonance) and HPLC which had been reported in previous studies (28). Therefore, DH-1 encodes an enzymatically active core-2 GlcNAc-T.

Figure 8:
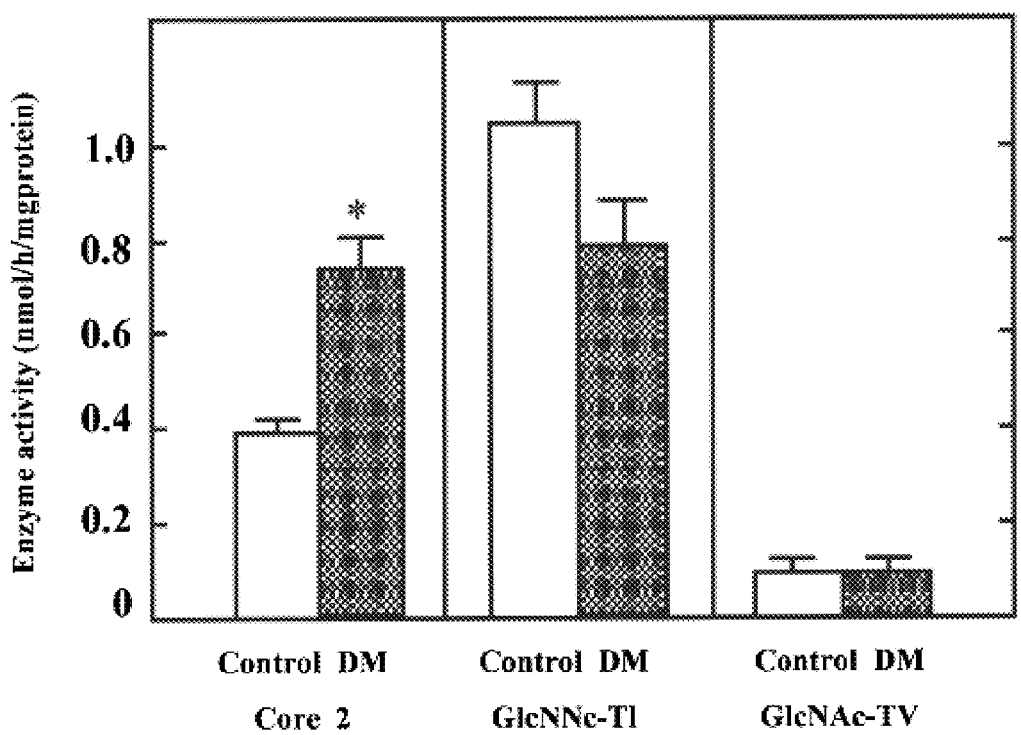
FIG. 8 are graphs showing core GlcNAc-T, GlcNAc-T1, and GlcNAc-TV activities in the heart of control (closed column) and two week diabetic rats.

GlcNAc-T activity in heart. With the identification of DH1 being an enzyme involved in mediating the biosynthesis of O-linked sugar chains, the specificity of the diabetes effect was tested by measuring the activities of core 2 GlcNAc-T (which branches maturing O-linked sugar chains) and two other GlcNAc transferases (which are specific for branching N-linked sugar chains) in the hearts of control and diabetic rats (FIG. 8). Core 2 GlcNAc-T activity increased significantly and specifically in diabetic hearts by 82% of, control (0.39±0.03 vs 0.71±0.10 nmol/h per mg protein n=3, P<0.05). In contrast, GlcNAc-TI and GlcNAc-TV activities were not significantly different between control and diabetes (GlcNAc-TI:1.05±0.11 vs 0.79±0.09 nmol/h per mg protein, GlcNAc-TV:0.078±0.024 vs 0.077±0.023 nmol/h per mg protein). The changes thus seem restricted to O-glycosylation.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

FULL CITATIONS FOR REFERENCES REFERRED TO IN THE SPECIFICATION

1. Kessler, I. I. 1971. Mortality experience of diabetic patients. *Am. J. Med.* 51:715–724.

2. Rubler. S., J. Dlugash, Y. Z. Yuceoglu, T. Kumral, A. W. Branwood, and A. Girshman. 1972. New type or cardiomyopathy associated with diabetic glomerulosclerosis. *Am. J. Cardiol* 30:595–602.

3. Kannel, W. B., M. Hjoltland, and W. P. Castelli. 1974. Role of diabetes in congestive heart failure: the Framingham study. *Am J. Cardiol.* 14:29–34.

4. Lababidi, Z. A., and D. E. Goldstein. 1983. High prevalence of echocardiographic abnormalities in diabetic youths. *Diabetes Care.* 6:18–22.

5. Reagan, T. J., P. O. Ettinger, M. I. Khan, M. U. Jesrani, M. M. Lyons, H. A. Oldewurtel, and M. Weber. 1974. Altered myocardial function and metabolism in chronic diabetes mellitus without ischemia in dogs. *Circ. Res.* 35:222–237.

6. Fein, F. S., J. E. Strobeck, A. Malhotra, J. Scheuer, and E. H. Sonnenblick. 1981. Reversibility of diabetic cardiomyopathy with insulin in rats. *Circ. Res.* 49:1251–1261.

7. Nishio, Y., A. Kashiwagi, Y. Kida, M. Kodama, N. Abe, Y. Saeki, and Y. Shigeta. 1988. Deficiency of cardiac B-adrenergic receptor in streptozocin-induced diabetic rats. *Diabetes.* 37:1181–1187.

8. Reagan, T. J., M. M. Lyons, S. S. Ahmed, G. E. Levinson, H. A. Oldewurtel, M. R. Ahmad, and B. Haider. 1977. Evidence for cardiomyopathy in familial diabetes mellitus. *J. Clin. Invest.* 60:885–899.

9. Factor, S. M., T. Minase, and E. H. Sonnenblick. 1980. Clinical and morphological features of human hypertensive-diabetic cardiomyopathy. *Am. Heart J.* 99:446–458.

10. Engerman, R. J., and T. S. Kern. 1987. Progression of incipient diabetic retinopathy during good glycemic control. *Diabetes.* 36:808–812.

11. Inoguchi, T., R. Battan, E. Handler, J. R. Sportsman, W. Heath, and G. L. King. 1992. Preferential elevation of protein kinase C isoform BII and diacylglycerol level in the aorta and heart of diabetic rats: differential reversibility to glycemic control by islet cell transplantation. *Proc. Natl. Acad. Sci. USA.* 89:11059–11063.

12. Nishio. Y., A. Kashiwagi, T. Ogawa, T. Asahina, M. Ikebuch, M. Kodama, and Y. Shigeta. 1990. Increase in [$^3$H] PN200-110 binding to cardiac muscle membrane in streptozocin-induced diabetic rats. *Diabetes.* 39:1064–1069.

13. Cagliero. E., M. Maiello, D. Boeri, S. Roy, and M. Lorenzi. 1988. Increased expression of basement membrane components in human endothelial cells cultured in high glucose. *J. Clin. Invest.* 82:735–738.

14. Ayo, S. H, R. A. Radink, W. F. Glass II, J. A. Garoni, E .R. Rampt, D. R. Appling, and J. L. Kreisberg. 1990. Increased extracellular matrix synthesis and mRNA in mesangial cells grown in high-glucose medium. *Am. J. Pathol.* 136:1339–1348.

15. Liang, P., and A. B. Pardee. 1992. Differential display of eukaryotic messenger RNA by means of polymerase chain reaction. *Science (Wash. D.C.)* 257:967–971.

16. Liang, P., L. Averboukh, K. Keyomarsi, R. Sager, and A. B. Pardee. 1992. Differential display and cloning of messenger RNAs from human breast cancer versus mammary epithelial cells. *Cancer Res.* 52:6966–6968.

17. Nishio, Y., L. P. Aiello, and G. L. King. 1994. Glucose induced genes in bovine aortic smooth muscle cells identified by mRNA differential display. *FASEB (Fet. Am. Soc. Exp. Biol.)J.* 8:103–106.

18. Aiello, L. P., G. S. Robinson, Y. W. Lin, Y. Nishio, and G. L. King. 1994. Identification of multiple glucose-regulated genes in bovine retinal pericytes by mRNA differential display. *Proc. Natl. Acad. Sci. USA.* 91:6231–6235.

19. Ikegami, H. G. S. Eisenbarth, and M. Hattori. 1991. Major histocompatibility complex-linked diabetogenic gene of the nonobese diabetic mouse. Analysis of genomic DNA amplified by the polymerse chain reaction. *J. Clin. Invest.* 85:18–24.

20. Klickstein, L. B., and L. R. Nerve 1991. Construction of recombinant DNA libraries. In Current Protocols in Molecular Biology. F. M. Ausubel. R. Brent, R. E. Kingston, D. D. Moore, J. G. Seidman, J. A. Smith, and K. Struhl, editors. John Wiley & Sons, New York. 5.0.1–5.6.10.

21. Maniatis, T., E. F. Fritsh, and J. Sambrook. 1982. Molecular Cloning. Cold Spring Harbor Laboratory, Cold Spring, N.Y.

22. Dennis, J. W. 1985. Different metastatic phenotypes and two genetic classes of wheat germ agglutinin-resistant tumor cell mutants. *Cancer Res.* 46:4594–4600.

23. Weis, J. H. 1991. Plating and transferring cosmid and plasmid library. In Current Protocols in Molecular Biology. F. M. Ausubel, R. Brent, R. E. Kingston, D. D. Moore, J. G. Siedman, J. A. Smith, and K. Struhl, editors. John Wiley & Sons, New York. 6.2.1–6.2.3.

24. Feigner, P. L., T. R. Gadek, M. Holm, R. Roman, H. W. Chan, M. Wenz, J. P. Northrup, G. M. Ringold.,and M. Danielsen. 1987. Lipofection: a highly efficient, lipid-mediated DNA transfection procedure. *Proc. Natl. Acad. Sci. USA.* 84:7413–7417.

25. Buczek-Thomas, J. A., S. R. Jaspers, and T. B. Miller, Jr. 1992. Adrenergic activation of glycogen phosphorylase in primary culture diabetic cardiomyocytes. *Am. J. Physiol.* 262:H649–H653.

26. Willams, D., and H. Schachter. 1980. Mucin synthesis. I. Detection in canine submaxillary glands of an N-acetyglucosaminyltransferase which acts on mucin substrates. *J. Biol. Chem.* 255:11247–11252.

27. Datti, A., and J. W. Dennis. 1993. Regulation of UDP-GlcNAc:GalB1-3GalNac-R B1-6-N-acetylglucosaminyltransferase (GlcNAc to GalNac) in Chinese hamster ovary cells. *J. Biol. Chem.* 268:5409–5416.

28. Yousefi, S., E. Higgins, Z. Doaling, O. Hindsgaul, A. Pollex-Kruger, and J. W. Dennis. 1991. Increased UDP-GlcNAc:Gal B1-3GalNAc-R (GlcNAc to GalNac) B1-6 N-acetylglucosaminyltransferase activity in transformedand metastatic murine tumor cell lines: control of polylactosamine synthesis. *J. Biol. Chem.* 266:1772–1783.

29. Moller, G., F. Reck, H. Paulsen, K. J. Kaur, M. Sarkar, H. Schachter, and L. Brockhausen. 1992. Control of glycoprotein synthesis: substrate specificity for rat liver UDP-GlcNAc:Manα3R B2-N-acetylglucosaminyl-transferase I using synthetic substrate analogues. *Glycoconj. J.* 9:180–190.

30. Kobayashi, M., T. Seki, K Yaginuma, and K. Koike. 1981. Nucleotide sequences of small ribosomal RNA and adjacent transfer RNA genes in rat mitochondrial DNA. *Gene.* 16:297–307.

31. Carvener, D. R., and S. C. Ray. 1991. Eukaryotic start and stop translation sites. *Nucleic Acids Res.* 19:3185–3192.

32. Bierhuizen. M. F., and M. Fukuda. 1992. Expression cloning of a cDNA encoding UDP-GlcNAc:GalB1-3GalNAc-R(GlcNAc to GalNAc) B1-GlcNAc transferase by gene transfer into CHO cells expressing polyoma large tumor antigen. *Proc. Natl. Acad Sci. USA.* 89:9326–9330.

33. Ledet, T. 1961. Histological and histchemical changes in the coronary arteries of old diabetic patients. *Diabetologia.* 4:268–272.

34. Camps, M., A. Castello. P. Munoz, M. Monfar. X. Testar. M. Palacin, and A. Zorzano. 1992. Effect of diabetes and fasting on GLUT-4 (muscle/fat) glucose-transporter expression in insulin-sensitive tissue. Heterogeneous response in heart red and white muscle. *Biochem. J.* 282:765–772.

35. Zarain, H. A., K. Yano, V. Elimban, and N. S. Dhalla. 1994. Cardiac sarcoplasmic reticulum $Ca^{2+}$-ATPase expression in streptozotocin-induced diabetic rat heart. *Biochem. Biophys. Res. Commun.* 203:113–120.

36. Hsiao, Y. C., K. Suzuki, H. Abe, and T. Toyota. 1987. Ultrastructral alterations in cardiac muscle of diabetic BB Wistar rats. *Virchows. Arch. A. Pathol. Anat. Histopathol.* 411:45–52.

37. Reinila, A., and H. K. Akerblom. 1984. Ultrastructure of heart muscle in short-term diabetic rats: influence of insulin treatment *Diabetologia* 27:397–402.

38. Jackson. C. V., G. M. McGrath, A. G. Tahiliani. R V. Vadlamudi, and J. H. McNeill. 1985. A functional and ultrastructural analysis of experimental diabetic rat myocardium. Manifestation of a cardiomyopathy. *Diabetes.* 34:876–883.

39. Kuo. T. H., K. H. Moore, F. Giacomelli, and J. Wiener. 1983. Defective oxidative metabolism of heart mitochondria from genetically diabetic mice. *Diabetes.* 32:781–787.

40. Clayton, D. A. 1984. Transcription of the mammalian mitochondrial genome. *Annu. Rev. Biochem.* 53:573–594.

41. Lee, Y.-C., N. Kojima. E. Wada, N. Kurosawa, T. Nagboka, T. Hamamoto, and S. Tsuji. 1994. Cloning and expression of cDNA for a new type of Galβ1,3-GalNAc α2,3-Sialyltransferase. *J. Biol. Chem.* 269:10028–10033.

42. Sachs, A. B. 1993. Messenger RNA degradation in eukaryotes. *Cell.* 74:413–421.

43. Brockhausen, I., W. Kuhns, H. Schachter, K. L Matta, D. R. Sutherland, and M. A. Baker. 1991. Biosynthesis of O-glycans in leukocytes from normal donors and from patients with leukemia: Increase in O-glycan core 2 UDP-GlcNAc:GalB3GalNAc-R (GlcNAc to GalNAc) B(1–6)-N-acetylglucosaminyl-transferase in leukemic cells. *Cancer Res.* 51:1257–1263.

44. Saitoh, F., F. Piller, R. I. Fox, and M. Fukuda. 1991. T-lymphocytic leukemia expresses complex branched O-linked oligosaccharides on a major sialoglycoprotein, Leukosialin. *Blood* 77:1491–1499.

45. Piller, F., F. L. Deist, K. I. Weinberg, R. Parkman, and M. Fukuda 1991. Altered O-glycan synthesis in lymphocytes from patients with Wiskott-Aldrich Syndrome. *J. Exp. Med.* 173:1501–1510.

46. Roy, S., M. Maiello, and M. Lorenzi. 1994. Increased expression of basement membrane collagen in human diabetic retinopathy. *J. Clin. Invest.* 93:438–442.

47. Fukui, M., T. Nakamura. I. Ebihara, I. Shirato, Y. Tomino, and H. Koide. 1992. ECM gene expression and its modulation by insulin in diabetic rats. *Diabetes.* 41:1520–1527.

48. Shanker, R., W. E. Neeley, and W. H. Dillmann. 1986. Rapid effects of insulin on in vitro translational activity of specific mRNA in diabetic rat heart. *Am. J. Physiol.* 250:E558–E563.

49. Page. M. M., R. B. Smith. and P. J. Watkins. 1976. Cardiovascular effects of insulin. *Br. Med. J.* 1:430–432.

50. O'Brien. M. R., and D. K. Granner. 1990. PEPCK gene as model of inhibitory effects of insulin on gene transcription. *Diabetes Care.* 13:327–339.

51. Bornfeldt. K. E., A. Skottener. and H. J. Arnqvist. 1992. In vivo regulation of messenger RNA encoding insulin-like growth factor-I (IGF-I) and its receptor by diabetes, insulin and IGF-I in rat muscle. *J. Endocrinol.* 135:203–211.

52. Dillmann, W. H. 1989. Diabetes and thyroid-hormone-induced changes in cardiac function and their molecular basis. *Annu Rev. Med.* 40:373–394.

We claim:

1. A method of preventing or treating cardiomyopathy associated with diabetes and hyperglycemia in a subject comprising reducing UDP-GlcNAc:Galβ1-3GalNAcαR β1-6-N-acetylglucosaminyl transferase (core 2 GlcNAc-T) activity in the subject by administering to the subject a substance that inhibits core 2 GlcNAc-T activity.

2. A method as claimed in claim 1, wherein the substance is an antisense sequence of a nucleic acid sequence encoding a protein with core 2 GlcNAc-T activity.

3. A method as claimed in claim 2, wherein the substance is an antisense nucleic acid molecule of a core 2 GlcNAc-T sequence as shown in FIG. 9 or GenBank Accession Nos. L41415, U41320, or U19265.

4. A method as claimed in claim 2, wherein the substance is an inhibitor of UDP-Gal:GalNAcαRβ1-3 galactosyltransferase or UDP-GalNAc:Ser/thr αN-acetylgalactosyltransferase.

5. A method as claimed in claim 1, wherein the substance is an analog of an acceptor substrate for core 2 GlcNAc-T.

6. A method as claimed in claim 5, wherein the substance is Galβ1-1GalNAcα.

7. A method as claimed in claim 1, wherein the substance which inhibits core 2 GlcNAc-T activity is a substance identified by (a) reacting core 2 GlcNAc-T with an acceptor substrate and a sugar nucleotide donor in the presence of the substance, under conditions whereby the core 2 GlcNAc-T produces a reaction product; (b) determining the amount of reaction product; and (c) comparing the amount of reaction product to an amount obtained for a control in the absence of the substance, whereby lower amounts of reaction product with the substance identify the substance as an inhibitor of core 2 GlcNAc-T activity.

8. A method as claimed in claim 1, wherein the substance which inhibits core 2 GlcNAc-T activity is a substance identified by (a) treating a cell which expresses core 2 GlcNAc-T with the substance; (b) assaying for Galβ1-3GalNAcα-associated with the cell; and (c) comparing the amount of Galβ1-3GalNAcα-associated with the cell to an amount associated with a control cell in the absence of the substance, whereby lower amounts of Galβ1-3GalNAcα-associated with the cell identify the substance as an inhibitor of core 2 GlcNAc-T activity.

9. A method as claimed in claim 1, wherein the substance which inhibits core 2 GlcNAc-T activity is an inhibitor of transcription or translation of a gene encoding a protein with core 2 GlcNAc-T activity.

10. A method as claimed in claim 1, wherein the substance which inhibits core 2 GlcNAc-T activity is an inhibitor of translation of a gene encoding a protein with core 2 GlcNAc-T activity.

* * * * *